United States Patent [19]

Horrobin

[11] Patent Number: 4,888,326
[45] Date of Patent: Dec. 19, 1989

[54] METHOD OF TREATING DEFECTIVE T-LYMPHOCYTE FUNCTION WITH RUTIN OR TROXERUTIN IN COMBINATION WITH γ-LINOLENIC ACID OR DIHOMO-γ-LINOLENIC ACID

[75] Inventor: David F. Horrobin, Montreal, Canada

[73] Assignee: Efamol Ltd., London, England

[21] Appl. No.: 168,603

[22] Filed: Mar. 4, 1988

[51] Int. Cl.$^4$ ............................................. A61K 31/70
[52] U.S. Cl. ...................................... 514/27; 514/558
[58] Field of Search ...................... 536/8; 514/27, 558

[56] References Cited

U.S. PATENT DOCUMENTS 4,211,772  7/1980  Fauran et al. .................... 536/8
4,309,415  1/1982  Horrobin ......................... 424/318

OTHER PUBLICATIONS

Lamber et al., Chemical Abstracts, vol. 93, 1980 No. 197805r.
Rote Liste, 1961, Bundesverband der Pharmazeutischen Industrie e.V. pp. 540, 541, 922 and 1050.

Primary Examiner—Ronald W. Griffin
Assistant Examiner—Elli Peselev
Attorney, Agent, or Firm—Nixon & Vanderhye

[57] ABSTRACT

A pharmaceutical composition comprises one or more essential fatty acids, for example, γ-linolenic acid or dihomo-γ-linolenic acid, in conjunction with rutin, troxerutin or other bioflavonoid. The composition is useful in the treatment of inflammation or defective T-lymphocyte function.

2 Claims, No Drawings

METHOD OF TREATING DEFECTIVE T-LYMPHOCYTE FUNCTION WITH RUTIN OR TROXERUTIN IN COMBINATION WITH γ-LINOLENIC ACID OR DIHOMO-γ-LINOLENIC ACID

This is a continuation of application Ser. No. 925,454, filed Oct. 31, 1986, now abandoned, which is a continuation of Ser. No. 632,699, filed July 23, 1984, now abandoned, which is a continuation of Ser. No. 487,762, filed Apr. 22, 1983, now abandoned.

FIELD OF THE INVENTION

This invention relates to compositions for and methods of combating the physical manifestations of ageing, especially inflammatory disorders or defective T-lymphocyte function primarily, but not exclusively, in the field of human medicine.

GENERAL BACKGROUND

Considerable interest has been shown in recent years in the use of prostaglandin (PG) precursors in medicine.

For various reasons it is not practical to administer naturally-occurring prostaglandins such as PGE 1 and PGE 2 to patients. Consequently, considerable attention has focussed on the use of prostaglandin precursors including linoleic acid (9,12-octadecadienoic acid), γ-linolenic acid (6,9,12-octadecatrienoic acid) and dihomo-γ-linolenic acid (5,8,11-eicosatrienoic acid), conversion in the body being believed to be as follows:

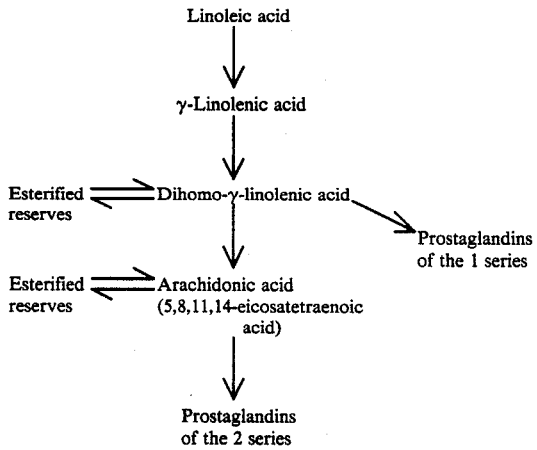

Ageing is characterised by a number of changes in body structure, physiology and biochemistry. There are for example increased susceptibilities to cardiovascular diseases and cancer. One of the key features of ageing is loss of the normal behaviour of the immune system. The body's immune system, usually directed outwards to invading organisms, becomes increasingly directed inwards, attacking the body's own substance. This immune failure appears to be due to progressive malfunction of cells known as T-lymphocytes and especially of a subset of these cells known as T suppressor lymphocytes (R. L. Walford, Amer. J. Clin. Pathol. 74: 247, 1980).

Many attempts have been made to prolong life in both human and animal experiments but only one technique has proved consistently if modestly successful. In several different studies, a reduced total food intake has been found to prolong animal life and to slow down the development of the abnormalities of the immune system (R. L. Walford, Amer. J. Clin. Pathol. 74: 247, 1980). The way in which food restriction works is unknown.

It is suggested by the present inventor that a key factor in the development of ageing is loss of the ability of the body to make γ-linolenic acid (GLA) from dietary cis-linoleic acid. Thus, by-passing this block by providing GLA directly, for example by mouth, by inunction through the skin, or by injection will slow down or prevent some of the processes of ageing and even reverse to some extent changes which have already occurred. Similar effects will be achieved by providing DGLA, to which GLA is rapidly converted in the body.

The evidence is as follows:

1. The ability of animals' tissues to convert linoleic acid to GLA falls with age. The rates at which this happens differ from organ to organ. In the rat testis the ability to make GLA is sharply reduced within a few months whereas in the rat liver it falls only after about one year. (S. Ayala et al, J. Lipid Res. 14: 296, 1973: R. O. Peluffo et al, Am. J. Physiol. 218: 669, 1970).

2. A loss of the ability to make GLA of course leads to loss of the ability to make further metabolites of GLA, notably PGE 1. PGE 1 is necessary for T-lymphocyte function and a lack of it is an explanation for the T-lymphocyte failure seen in ageing. PGE 1 also lowers cholesterol levels, lowers blood pressure and reduces the risk of thrombosis (D. F. Horrobin, Med. Hypotheses 6: 785–800, 1980): a lack of it is an explanation for the increased risk of diseases of the heart and circulation with ageing. PGE 1 in laboratory animals can normalise cancer cells (D. F. Horrobin, Med. Hypotheses 6: 469, 1980) and a lack of PGE 1 is an explanation for the increased risk of cancer with ageing.

3. In experiments designed to look at the effects of calorie restriction on essential fatty acid metabolism, moderate calorie restriction in rats increased by over 300% the ability of the animals to convert linoleic acid to GLA (Faas et al, Lipids 15: 953–61, 1980).

4. High alcohol intake (D. F. Horrobin, Med. Hypotheses 6: 929, 1980) and diabetes (R. R. Brenner, Molecular Cellular Biochem 3: 41, 1974) both lead to loss of the ability to convert linoleic acid to GLA. Both are also associated with a risk of accelerated ageing.

5. GLA in the form of Evening Primrose oil has been found to correct defects which can be associated with ageing:

(a) GLA in the form of Evening Primrose oil has improved the clinical status of humans with eczema and with Sjögren's syndrome and of animals with adjuvant arthritis. All these conditions are associated with defective T-lymphocyte function.

(b) GLA in the form of Evening Primrose oil can lower blood pressure and blood cholesterol. Elevated blood pressure and cholesterol are commonly associated with ageing.

Thus a number of factors have led the present inventor to propose that development of the above and other physical manifestations of ageing may be slowed down or stopped, and some even reversed, by the provision of adequate amounts of either GLA or DGLA. However such a proposal, while new in the sense of giving the GLA or DGLA for a new purpose, is something that has been done before for other reasons. Everyone is ageing, and, among at least the older people given the acids, there will have been some showing the physical manifestations of ageing discussed.

The inventor however specifically believes that among the numerous recognised essential nutrients rutin, troxerutin and other bioflavonoids have a particularly significant effect in the ageing content. Rutin has the specific action in both the 1-series and 2-series of blocking the conversion of PGE to PGF. There is substantial evidence that PGE's (especially PGE 1) are the most desirable PG's in the body, compared for example to the related thromboxanes which tend to be toxic and the other PG's which have mixed good and bad effects, and this is especially so in the ageing context. The specific effect of rutin in blocking a route by which PGE's are lost is thus highly significant.

Thus the present invention lies in compositions and use of essential fatty acids, and most particularly $\gamma$-linolenic acid and dihomo-$\gamma$-linolenic acid and physiologically functional derivatives thereof, with materials blocking PGE to PGF conversion, particularly rutin, troxerutin and other bioflavonoids, either as such or (as is discussed further herein) in conjunction with zinc, $\beta$-lactam antiobiotics or other materials influencing the 1-series/2-series PG balance in the body in favour of 1-series PG's, herein referred to as 1-series PG enhancers.

The 1-series PG enhancers are discussed at length in the present inventor's published European Patent Specifications Nos. 0 003 407 (zinc and $\beta$-lactam antibiotics), 0 004 770 (penicillamine, phenformin or levamisole and a group of other materials including colchicine and vinca alkaloids); and 0 019 423 (Vitamin C, ethyl alcohol, and opiate antagonists). The disclosure of these specifications, both as to materials proposed and as to amounts suitable for administration, for use in conjunction with $\gamma$-linolenic acid or dihomo-$\gamma$-linolenic acid, is incorporated herein by reference. Not all of the materials, of course, would be materials of choice in view of their other effects, but they are nevertheless effective in the present context.

Amounts in which rutin, troxerutin and other bioflavonoids may suitably be administered are for example 10 mg-10 g daily preferably 50-250 mg. Amounts for other materials are discussed elsewhere herein. For the essential fatty acids, calculations as to what doses are likely to be adequate are based on what is known about linoleic acid requirements. In young animals and humans a minimum of 1% of total calorie intake is desirable in the form of linoleic acid. Many authorities have argued that this is too low, especially for normal brain and immune function and have suggested that 5% of total calorie intake of linoleic acid is required. The following calculations have assumed that most of this linoleic acid can be converted to GLA under normal conditions in young animals and that with ageing the body may totally lose its ability to make GLA. 2.2 grams of GLA would provide 20 calories or 1% of the calorie intake of an adult eating 2000 calories worth per day. 22 grams of GLA would provide 200 calories or 5% of the calorie intake of an adult eating 4000 calories per day. If the body is producing no GLA even a small amount may be helpful and the suggested minimum daily dose is therefore 20 to 50 mg. On the other hand there could be losses for one reason or another and the suggested maximum dose is 10 to 100 grams. The preferred dose range is 1 gram to 10 grams per day. DGLA or esters or other derivatives of GLA or DGLA can be used instead, when the above amounts shall be recalculated but on the GLA equivalent.

DIETARY COMPOSITIONS

The invention is chiefly described in terms of pharmaceutical use, but it will be understood that the $\gamma$-linolenic and other acids, being in the nature of dietary supplements, could if available at an economic price be incorporated in a dietary margarine or other foodstuff; such dietary approaches are within the purview of the invention.

VETERINARY APPLICATIONS

It will be understood that where a disorder of a kind calling for treatment in animals arises, the invention while described primarily in terms of human treatment is equally applicable in the veterinary field.

FORMS AND SOURCES OF $\gamma$-LINOLENIC AND OTHER ACIDS

Suitable physiologically functional derivatives, convertible in the body to GLA or DGLA to enter the biosynthetic pathway given earlier herein, are physiologically acceptable salts, esters (particularly glycerides and simple $C_1$-$C_4$ alkyl esters), amides and phospholipids. Indirect identification of useful derivatives is by their having the valuable effect in the body of the acid (GLA or DGLA) itself, but conversion can be shown directly by gas chromatographic analysis of GLA or DGLA concentration in blood, body fat, or other tissue by standard techniques for example those of Pelick et al. p.23, "Analysis of Lipids and Lipoproteins" Ed. Perkins, American Oil Chemists Society, Champaign, Ill., U.S.A.

If desired, compositions may be produced for use in the invention by associating natural or synthetic $\gamma$-linolenic acid (or a physiologically functional derivative thereof) and/or dihomo-$\gamma$-linolenic acid (or a physiologically functional derivative thereof) as such, with an acceptable pharmaceutical vehicle. It will however generally be convenient to incorporate the $\gamma$-linolenic acid into compositions in the form of an available oil having a high $\gamma$-linolenic acid content.

At the present time known natural sources of oils having a high $\gamma$-linolenic acid content are few (there are no known natural sources of significant amounts of dihomo-$\gamma$-linolenic acid). One source of oils currently available is the seed of Evening Primrose species such as *Oenothera biennis L.* and *Oenothera lamarckiana*, the oil extract therefrom containing $\gamma$-linolenic acid and linoleic acid in the form of their glycerides together with other glycerides. Another source of $\gamma$-linolenic acid is the seed of Borage species such as *Borago officinalis* which, though its current yield per acre is low, provides a richer source of $\gamma$-linolenic acid than Oenothera oil. Recent studies on fungi which can be cultivated by fermentation promise a fungal oil source.

The seed oil extracts referred to above can be used as such or can if desired be fractionated to yield an oily composition containing the triglycerides of $\gamma$-linolenic acid and linoleic acid as the only fatty acid components, the $\gamma$-linolenic acid content being a major proportion. Seed oil extracts appear to have a stabilising effect upon any dihomo-$\gamma$-linolenic acid or physiologically functional derivative thereof incorporated therein.

PHARMACEUTICAL PRESENTATION

The compositions administered in use of the invention are conveniently in a form suitable for oral, rectal, parenteral or topical administration in a suitable pharmaceutical vehicle, as discussed in detail for example in U.K. Patent Specification No. 1 082 624 and in any case known generally according to the type of preparation. Thus for example tablets, capsules, ingestible liquid or powder preparations, creams and lotions for topical application, or suppositories, can be prepared as required.

Advantageously a preservative such as $\alpha$-tocopherol is incorporated into the preparations. $\alpha$-Tocopherol in a concentration of about 0.1% by weight has been found suitable for the purpose.

It will be understood that the absolute quantity of active ingredients present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

The following Examples serve to illustrate compositions useful according to the invention:

EXAMPLES

Pharmaceutical compositions containing a unit dose of an oil extract from the seeds of *Oenothera biennis L.* optionally with methyl dihomo-$\gamma$-linolenate are prepared by encapsulation of the natural oil in soft gelatin capsules manufactured by known methods, incorporating rutin also.

The oil is extracted from the seeds by one of the conventional methods of extraction such as cold pressure, screw pressure after partially cooking the seed, or solvent extraction.

Fractionation of a typical sample of this oil shows a yield of 97.0% oil in the form of methyl esters, with the relative

| portions: | |
|---|---|
| Palmitate | 6.15 |
| Stearate | 1.6 |
| Oleate | 10.15 |
| Linoleate | 72.6 |
| $\gamma$-Linolenate | 8.9 |

As preservative, $\alpha$-tocopherol is added to the oil in a concentration of 0.1%.

Gelatin capsules containing oil extracts prepared as described above, each having the following contents of active ingredients (0.5 g oil extract=ca 0.045 g $\gamma$-linolenic acid), are prepared in conventional fashion.

EXAMPLE 1

| Oil extract | 1.5 g |
|---|---|
| Rutin | 25 mg |

Five capsules may be administered four times daily in combating the manifestations of ageing discussed herein, especially inflammatory disorders and defective T-lymphocyte function, giving a daily dose of $\gamma$-linolenic acid of ca 2.7 g.

EXAMPLE 2

| Oil extract | 1.5 g |
|---|---|
| Methyl dihomo-$\gamma$-linolenate | 20 mg |
| Rutin | 20 mg |

Capsules may be administered daily as above.

Alternatives to the above are capsules containing a fraction of the natural oil, rich in $\gamma$-linolenate, allowing fewer or smaller capsules for the same dose of $\gamma$-linolenate or the administration of larger doses thereof without inconvenience.

What is claimed is:

1. A method of treating defective T-lymphocyte function comprising administering to a person requiring same effective amounts of rutin or troxerutin with gamma-linolenic acid or dihomo-gamma-linolenic acid.

2. The method according to claim 1 wherein said amounts are, daily, 0.05 to 10 g of said $\gamma$-linolenic acid or molar equivalent amount of said dihomo-$\gamma$-linolenic acid and 10 mg to 10 g of said rutin or troxerutin.

* * * * *